United States Patent [19]
Reuter et al.

[11] 4,430,504
[45] Feb. 7, 1984

[54] SILYL ETHERS, A PROCESS FOR THEIR PRODUCTION AND THEIR USE AS POLYMERIZATION INITIATORS

[75] Inventors: Knud Reuter; Rolf Dhein, both of Krefeld, Fed. Rep. of Germany

[73] Assignee: Bayer Aktiengesellschaft, Leverkusen, Fed. Rep. of Germany

[21] Appl. No.: 448,732

[22] Filed: Dec. 10, 1982

[30] Foreign Application Priority Data

Dec. 24, 1981 [DE] Fed. Rep. of Germany ....... 3151444

[51] Int. Cl.$^3$ ............................ C07F 7/08; C07F 7/18
[52] U.S. Cl. .................................. 556/482; 526/174; 526/194
[58] Field of Search ................. 556/443, 482; 526/194

[56] References Cited

U.S. PATENT DOCUMENTS 3,162,663 12/1964 Beck ................................... 556/482
4,251,650 2/1981 Mietzch et al. ..................... 326/194

FOREIGN PATENT DOCUMENTS 1156257 6/1969 United Kingdom ............... 556/443

Primary Examiner—Joseph L. Schofer
Assistant Examiner—Peter F. Kulkosky
Attorney, Agent, or Firm—Connolly and Hutz

[57] ABSTRACT

Silyl ethers obtainable from aryl silyl ketones and mono-, di-, tri- or tetra-chlorosilanes in the presence of base metals are eminently suitable for use as initiators for radical polymerization reactions.

4 Claims, No Drawings

SILYL ETHERS, A PROCESS FOR THEIR PRODUCTION AND THEIR USE AS POLYMERIZATION INITIATORS

This invention relates to new silyl ethers obtainable by reacting aryl silyl ketones with base metals and mono- di- tri- or tetra-chlorosilane, to a process for their production and to their use as initiators for radical polymerisation reactions.

On account of the known dangers of polymerisation initiators containing peroxide groups, 1,1,2,2-tetraaryl-1,2-dihydroxy ethanes and their alkyl and silyl ethers have already been proposed as initiators for thermally initiated radical polymerisation reactions (DE-AS No. 12 16 877, DE-AS No. 12 19 224 and DE-OS Nos. 21 31 623 and 21 64 482). Initiators of the 1,2-diaryl-1,2-dicyano-1,2-dihalogen ethane type (DE-OS No. 24 44 252), the 1,2-diaryl-1,1,2,2-tetracarbalkoxy ethane type (US-PS No. 3,896,099) and the 1,2-diaryl-1,1,2,2-tetramethyl ethane type containing partly chlorinated methyl groups (BE-PS No. 834,599) are also known. Silyl ethers of oligomers containing recurring units having the following structure:

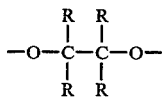
(I)

in which R represents phenyl or alkyl, are known as suitable for initiating polymerisation reactions (DE-OS Nos 26 32 294 and 26 56 782).

It is also known that certain substituted tartaric acid esters can be used as radical initiators for polymerisation reactions (DE-OS Nos 28 53 938 and 29 09 951).

There was a need for initiators free from peroxide groups which are stable in storage at room temperature in the compounds or mixtures to be polymerised, are superior in their reactivity at elevated temperatures to known peroxide-free initiators even in very low concentrations in the polymerisable system, and give thoroughly hardened products with very little colour of their own.

It has now surprisingly been found that the silyl ethers of 1,2-diphenyl-1,2-disilyl ethane-1,2-diols defined in the following meet these requirements. In addition, they have the advantage that, on decomposing into radicals, they do not release any volatile fragments which could produce undesirable bubble formation in the polymer.

The present invention provides silyl ethers corresponding to the following formula (II):

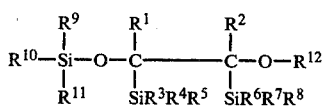
(II)

in which $R^1$ and $R^2$ represent $C_6$–$C_{12}$ aryl radicals optionally substituted by $C_1$–$C_4$-alkyl (preferably methyl), by methoxy, chlorine or fluorine, preferably phenyl, tolyl, p-tert.-butyl phenyl, o- and p-chlorophenyl, 2,4-dichlorophenyl, naphthyl, biphenylyl, m-methoxyphenyl, $R^3$ to $R^8$, independently of one another represent, methyl, ethyl, phenyl or benzyl groups, $R^9$ represents methyl, ethyl, phenyl, benzyl, chloromethyl or a group A, $R^{10}$ represents chlorine, hydroxyl, methoxy, ethoxy, $R^9$ or a group A, $R^{11}$ represents chlorine, hydroxyl, $R^9$ or a group A, $R^{12}$ represents a silyl radical corresponding to the following formula:

(III)

and A represents a radical corresponding to the following formula:

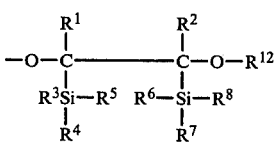
(IV)

the compounds of formula II optionally containing the partial structure:

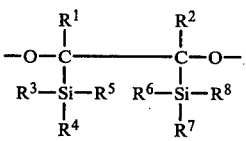
(V)

from one to twenty times, and mixtures of these compounds.

The present invention also provides a process for producing the silyl ethers of formula II which is characterised in that 1 mole of an aryl silyl ketone corresponding to the following formula (VI).

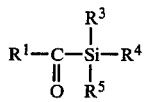

in which $R^1$, $R^3$, $R^4$ and $R^5$ are as previously defined, and substantially the equivalent quantity of a base metal, preferably about 0.5 mole of a metal of the 2nd Main Group of the Periodic System, such as magnesium or calcium, or about 1 mole of a metal of the 1st Main Group of the Periodic System, such as lithium, sodium or potassium, are reacted in an inert aprotic solvent at −10° to +70° C. and preferably at −5° to +50° C., if necessary while cooling, with about 1 mole of a monochloro-organosilane corresponding to the following formula (VII):

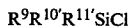
$R^9R^{10'}R^{11'}SiCl$ (VII)

or with from 0.4 to 0.8 mole and preferably with from 0.5 to 0.6 mole of a dichloro-organosilane corresponding to the following formula (VIII):

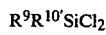
$R^9R^{10'}SiCl_2$ (VIII)

or with from 0.25 to 0.6 mole and preferably with from 0.3 to 0.4 mole of a trichloro-organosilane corresponding to the following formula (IX):

$$R^9SiCl_3 \qquad (IX)$$

or with from 0.1 to 0.7 mole of tetrachlorosilane until the exothermic reaction is over, the reaction product is hydrolysed, the organic phase is separated off and the solvent is removed under a pressure of from 2 to 6 Torr. In the above formulae, $R^9$ has the meaning defined above and $R^{10'}$ and $R^{11'}$ represent the same substituents as defined above for $R^{10}$ and $R^{11}$ apart from A.

The present invention also provides reaction mixtures obtainable by this process.

The present invention further provides the use of the reaction mixtures according to the invention as initiators for radical polymerisation reactions.

Providing the silyl ethers according to the invention are not produced solely from monofunctional chlorosilanes (VII), but oligomeric silyl ethers are obtained instead by using difunctional, trifunctional or even higher chlorosilanes, i.e. for example VIII, IX or tetrachlorosilane, these oligomeric silyl ethers have a molecular weight (determined as a number average) of from 500 to 12,000 and preferably from 2000 to 8000. They generally contain the partial structure (V) from 1 to 20 times.

The molecular weights of the silyl ethers according to the invention are determined by vapour pressure osmometry up to a molecular weight of 3000 and by membrane osmometry for molecular weights above 3000, in either case using acetone as solvent. The molecular weights of individual fractions of the reaction mixtures according to the invention may be determined by gel chromatography (using calibration substances).

Various reactants are mentioned in the following as examples of the combinations to be used preferably as starting materials:

| (1)  | magnesium | benzoyl trimethyl silane       | chlorotrimethyl silane         |
|------|-----------|--------------------------------|--------------------------------|
| (2)  | magnesium | benzoyl triphenyl silane       | chlorotrimethyl silane         |
| (3)  | magnesium | benzoyl trimethyl silane       | dichlorodimethyl silane        |
| (4)  | sodium    | benzoyl trimethyl silane       | chlorotrimethyl silane         |
| (5)  | lithium   | benzoyl trimethyl silane       | trichloromethyl silane         |
| (6)  | magnesium | benzoyl trimethyl silane       | trichloromethyl silane         |
| (7)  | magnesium | benzoyl triphenyl silane       | dichlorodimethyl silane        |
| (8)  | magnesium | benzoyl dimethyl phenyl silane | chlorotrimethyl silane         |
| (9)  | magnesium | 4-methyl benzoyl trimethyl silane | chlorotrimethyl silane      |
| (10) | magnesium | 3-methyl benzoyl methyl silane | chlorotrimethyl silane         |
| (11) | potassium | 2-methyl benzoyl trimethyl silane | dichlorodimethyl silane     |
| (12) | calcium   | benzoyl triphenyl silane       | dichlorodimethyl silane        |
| (13) | magnesium | benzoyl trimethyl silane       | tetrachlorosilane              |
| (14) | magnesium | benzoyl trimethyl silane       | 1,2-dichlorotetramethyl disilane |
| (15) | magnesium | 4-methylbenzoyl trimethyl silane | 1,1,2-trichlorotrimethyl disilane |
| (16) | aluminium | benzoyl triphenyl silane       | tetrachlorosilane              |
| (17) | magnesium | benzoyl dimethyl phenyl silane | trichloromethyl silane         |
| (18) | sodium    | 4-chlorobenzoyl trimethyl silane | chlorotrimethyl silane       |
| (19) | magnesium | 2-chlorobenzoyl trimethyl silane | dichlorodimethyl silane      |
| (20) | magnesium | benzoyl triethyl silane        | chlorotrimethyl silane         |

Suitable inert aprotic solvents are, for example, aromatic compounds and aromatic alkyl compounds, such as benzene and toluene, ethers such as diethyl ether, diisopropyl ether, dibutyl ether, anisole, tetrahydrofuran, dioxane, 1,2-dimethoxy ethane, trialkyl phosphates, such as triethyl phosphate, tributyl phosphate; N,N-disubstituted amides, such as dimethyl formamide, N,N-dimethyl acetamide and phosphoric acid tris-(dimethylamide). Other suitable solvents are described in Methoden der Organischen Chemie (Houben-Wyl), Vol, XIII/2a, pages 59–70, Georg Thieme-Verlag, Stuttgart 1973. Solvent mixtures of from 0 to 80 parts by weight of benzene or toluene, 2 to 98 parts by weight of tetrahydrofuran and 2 to 98 parts by weight of triethyl phosphate or phosphoric acid tris-(dimethylamide) have proved to be particularly suitable. In order not to dilute the reaction mixture unnecessarily, as little solvent as possible is normally used. In general, an aryl silyl ketone:solvent ratio by weight of 1:1 is entirely adequate.

It is advisable to bear in mind the fact that, under the reaction conditions, partial decomposition can actually occur. If, therefore, the reaction mixture according to the invention should show some slight reactivity attributable to decomposition of the compounds acting as initiator during production, it is advisable to reduce the reaction temperature.

In some cases, the reaction mixtures according to the invention are actually active at temperatures above 40° C. Complete and rapid hardening is generally obtained when they are used in quantities of from 0.02 to 1% by weight and preferably in quantities of from 0.05 to 0.8% by weight, based on the substance to be polymerised.

The polymerisation reaction is initiated by heating a mixture of the substance to be polymerised and the reaction mixture according to the invention beyond a specific activation temperature which may readily be determined in each individual case. Radically polymerisable systems are generally hardened between 60° and 200° C.

Hardening may be carried out in a single stage or, if desired, even in several stages (cf. GB-PS No. 1,041,641).

The activation temperature of the initiator reaction mixtures according to the invention may be determined by a simple colour reaction: because the radicals formed during thermal decomposition are capable of decolouring quinoid dyes. To carry out the test, a small quantity of quinoid dye, for example methylene blue, thionine or neutral red, is dissolved in a solvent free from molecular oxygen, for example glycol, xylene, and an at least equivalent quantity of the reaction mixture according to the invention is added to the resulting solution. The temperature at which the dye is decoloured is the activation temperature of the initiator reaction mixture.

The polymerisation of any radically polymerisable compounds or mixtures may be initiated by the reaction mixtures according to the invention i.e. for example conjugated dienes such as butadiene, isoprene, chloroprene; vinyl chloride, vinylidene chloride; aromatic vinyl compounds, such as styrene, divinyl benzene;

vinyl esters, particularly vinyl acetate and vinyl propionate; vinyl ethers, such as vinyl propyl ether, vinyl isobutyl ether; acrylic acid and methacrylic acid and derivatives thereof, such as esters, particularly with aliphatic alcohols containing from 1 to 5 C-atoms, nitriles, amides, etc.; di(vinylphenyl)carbonates; diallyl phthalate, diallyl carbonate, diallyl fumarate; di(allylphenyl)carbonates; polyol poly(meth)acrylates; and N,N'-methylene-bis-(meth)accrylamide.

Particularly suitable substances for the initiation of polymerisation reactions using the reaction mixtures according to the invention are unsaturated polyester resins, i.e. solutions of $\alpha,\beta$-ethylenically unsaturated polyesters in monomers copolymerisable therewith.

Suitable $\alpha,\beta$-ethylenically unsaturated polyesters are the usual polycondensation products of at least one $\alpha,\beta$-ethylenically unsaturated dicarboxylic acid generally containing 4 or 5 C-atoms or ester-forming derivatives thereof, for example anydrides, optionally in admixture with up to 200 mole percent, based on the unsaturated acid components, of at least one aliphatic saturated dicarboxylic acid containing 4–10 C-atoms or a cycloaliphatic or aromatic dicarboxylic acid containig 8–10 C-atoms or ester-forming derivatives thereof, with at least one polyhydroxy compound, particularly a dihydroxy compound, containing 2 to 8 C-atoms, i.e. polyesters of the type described in "Polyesters and Their Applications" by J. Bjorksten et al, Reinhold Publishing Corp., New York, 1956.

Examples of preferred unsaturated dicarboxylic acids or their derivatives are maleic acid or maleic acid anhydride and fumaric acid. However, it is also possible to use, for example, mesaconic acid, citraconic acid, itaconic acid or chloromaleic acid. Examples of the aliphatic saturated, cycloaliphatic and aromatic dicarboxylic acids used and their derivatives are phthalic acid and phthalic acid anhydride, isophthalic acid, terephthalic acid, hexahydro- or tetrahydrophthalic acid, etc., their anhydrides, endomethylene tetrahydrophthalic acid or its anhydride, succinic acid or succinic acid anhydride and succinic acid esters and chlorides, adipic acid, sebacic acid. To produce flame-resistant resins, it is possible to use for examples hexachloroendomethylene tetrahydrophthalic acid, tetrachlorophthalic acid or tetrabromophthalic acid. Suitable dihydric alcohols are ethylene glycol, 1,2-propane diol, 1,3-propane diol, diethylene glycol, dipropylene glycol, 1,3-butane diol, 1,4-butane diol, neopentyl glycol, 1,6-hexane diol, 2,2-bis-(4-hydroxycyclohexyl)-propane, bis-alkoxylated bisphenol and others. It is preferred to use ethylene glycol, 1,2-propane diol, diethylene glycol and dipropylene glycol.

Further modifications may be made by the incorporation of mono-, tri- and tetrahydric alcohols containing from 1 to 6 C-atoms, such as methanol, ethanol, butanol, allyl alcohol, benzyl alcohol, cyclohexanol, and tetrahydrofurfuryl alcohol, trimethyl propane, glycerol and pentaerythritol, and of mono-, di- and triallyl ethers and benzyl ethers of trihydric and higher alcohols containing from 3 to 6 C-atoms according to DE-AS No. 10 24 654 and also by the incorporation of monobasic acids, such as benzoic acid, or long-chain unsaturated fatty acids, such as oleic acid, linseed oil fatty acid and ricinene fatty acid.

The acid numbers of the polyesters are usually between 1 and 100 and preferably between 20 and 70, their OH-numbers between 10 and 150 and preferably between 20 and 100 and their molecular weights (determined as number averages $\overline{M}_n$) between 500 and 5000 and preferably between 1000 and 3000 (as measured by vapour pressure osmometry in dioxane and acetone; in the event of differing values, the lower value is taken as the correct value).

Suitable vinyl and vinylidene compounds copolymerisable with the unsaturated polyesters are unsaturated compounds preferably containing $\alpha$-substituted vinyl groups or $\beta$-substituted allyl groups of the type commonly encountered in polyester technology, preferably styrene; also for example, nucleus chlorinated and -alkylated or -alkenylated styrenes, the alkyl groups containing from 1 to 4 C-atoms, for example vinyl toluene, divinyl benzene, $\alpha$-methyl styrene, tert.-butyl styrene, chlorostyrenes; vinyl esters of carboxylic acids containing from 2 to 6 carbon atoms, preferably vinyl acetate; vinyl pyridine, vinyl naphthalene, vinyl cyclohexane, acrylic acid and methacrylic acid and/or their esters (preferably vinyl, allyl and methallyl esters) containing from 1 to 4 carbon atoms in the alcohol component, their amides and nitriles, maleic acid anhydride, semi- and diesters containing from 1 to 4 C-atoms in the alcohol component, semi- and diamides or cyclic imides, such as N-methyl maleic imide or N-cyclohexyl maleic imide; ally compounds, such as allyl benzene, and allyl esters, such as allyl acetate, phthalic acid diallyl ester, isophthalic acid diallyl ester, fumaric acid diallyl ester, allyl carbonates, diallyl carbonate, triallyl phosphate and triallyl cyanurate.

The parts quoted in the following Examples are parts by weight and the percentages are percentages by weight.

EXAMPLE 1

17.8 g of benzoyl trimethyl silane (0.1 mole) and 1.3 g of magnesium (0.053 mole) were added to an anhydrous mixture of 50 g of triethyl phosphate and 50 g of toluene. 10.9 g of chlorotrimethyl silane (0.1 mole) were added dropwise at 30° C. and the mixture stirred at 30° to 35° C. until the magnesium had completely reacted. The fully reacted mixture was poured into 100 ml of ice water, the aqueous phase was removed and the organic phase was washed thoroughly with water. The toluene was removed in vacuo. 5.04 g of 1,2-bis-(trimethylsilyl)-1,2-bis-(trimethylsiloxy)-1,2-diphenyl ethane, M.p. 132°–133° C. (from methanol), gradually crystallized from the residue.

EXAMPLE 2

An unsaturated polyester resin produced from 11 parts of phthalic acid anhydride, 47 parts of maleic acid anhydride and 42 parts of 1,2-propylene glycol at 200° C. (acid number 20, OH- number 30, viscosity at 20° C.: 1500 cP) was dissolved to form a 66% solution in styrene. The resulting solution was stabilised with 0.01% of hydroquinone and mixed with 0.7% of the initiator of Example 1.

One hour after the addition of the initiator, 20 g of a resin mixture were introduced into a 16 mm diameter test tube. An iron-constantan thermocouple connected to a temperature-time recorder was immersed in the resin to a depth of 3 cm and, after the recorder had been switched on, the test tube filled to a level of 8 cm was placed in a thermostatically controlled oil bath. The hardening time $t_H$ (time taken to reach the peak temperature minus the time taken to pass the 65° C.-line) and the peak temperature ($t_m$) was determined in accordance with DIN 16 945.

The following values were obtained for the bath temperatures indicated:

| Bath Temperature (°C.) | $t_H$ (min) | $t_m$ (°C.) |
| --- | --- | --- |
| 80 | 14 | 205 |
| 90 | 11 | 220 |
| 100 | 7.5 | 245 |

The hardened compositions were substantially colourless.

We claim:

1. Silyl ethers corresponding to the formula:

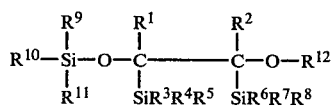
(II)

in which

R$^1$ and R$^2$ represent phenyl, tolyl, p-tert.-butyl phenyl, o- and p-chlorophenyl, 2,4-dichlorophenyl, or m-methoxyphenyl, R$^3$ to R$^8$ independently of one another represent methyl, ethyl or phenyl, R$^9$ represents methyl or A, R$^{10}$ and R$^{11}$ represent chlorine, methyl or A, R$^{12}$ represents a silyl radical corresponding to the formula:

(III)

and A represents a radical corresponding to the formula:

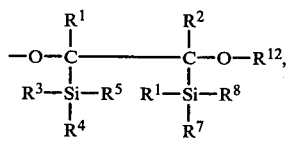
(IV)

the compounds of the formula II optionally containing the partial structure

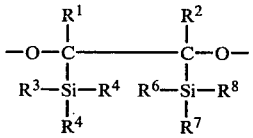
(V)

from one to twenty times.

2. A process for the production of silyl ethers, characterised in that 1 mole of an aryl silyl ketone corresponding to the formula:

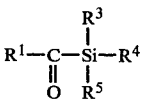

in which R$^1$, R$^3$, R$^4$ and R$^5$ are as defined in claim 1, and a substantially equivalent quantity of a base metal are reacted in an inert aprotic solvent at $-10°$ to $70°$ C. with about 1 mole of a monochloro-organosilane corresponding to the formula $$R^9R^{10'}R^{11'}SiCl \qquad (VII)$$

or with 0.4 to 0.8 mole of a dichloro-organosilane corresponding to the formula $$R^9R^{10'}SiCl_2 \qquad (VIII)$$

or with 0.25 to 0.6 mole of a trichloro-organosilane corresponding to the formula $$R^9SiCl_3 \qquad (IX)$$

or with 0.1 to 0.7 mole of a tetrachlorosilane until the exothermic reaction has ceased, the reaction product is hydrolysed, the organic phase is separated off and the solvent removed under a pressure of from 2 to 6 Torr; R$^9$ being as defined in claim 9 and R$^{10'}$ and R$^{11'}$ representing the same substituents as defined in claim 9 for R$^{10}$ and R$^{11}$ except for A.

3. A process as claimed in claim 2, characterised in that the reaction of the aryl silyl ketone (VI) is carried out at a temperature of $-5°$ to $50°$ C.

4. A process as claimed in claim 2, characterised in that 0.5 to 0.6 mole of the dichloro-organosilane (VIII) or 0.3 to 0.4 mole of the trichloro-organosilane (IX) or 0.1 to 0.7 mole of chlorine-containing polyorganosilane or siloxane having a molecular weight of from 150 to 1500 are used per mole of the aryl silyl ketone (VI).

* * * * *